United States Patent
Passeron et al.

(10) Patent No.: US 12,048,693 B2
(45) Date of Patent: *Jul. 30, 2024

(54) SUBSTITUTED HALO-QUINOLINE DERIVATIVES, METHOD OF PREPARATION AND APPLICATIONS THEREOF

(71) Applicants: Institut National de la Sante et de la Recherche Medicale (INSERM), Paris (FR); Centre National de la Recherche Scientifique, Paris (FR); Université Côte d'Azur, Nice (FR)

(72) Inventors: Thierry Passeron, Nice (FR); Rachid Benhida, Nice (FR); Pascal Dao, Nice (FR); Gian Marco De Donatis, Nice (FR); Anthony Martin, Nice (FR)

(73) Assignees: CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); UNIVERSITÉ CÔTE D'AZUR, Nice (FR)

( * ) Notice: Subject to any disclaimer, the term of this patent is extended or adjusted under 35 U.S.C. 154(b) by 713 days.

This patent is subject to a terminal disclaimer.

(21) Appl. No.: 16/959,954

(22) PCT Filed: Jan. 4, 2019

(86) PCT No.: PCT/EP2019/050175
§ 371 (c)(1),
(2) Date: Jul. 2, 2020

(87) PCT Pub. No.: WO2019/134975
PCT Pub. Date: Jul. 11, 2019

(65) Prior Publication Data
US 2020/0361872 A1  Nov. 19, 2020

(30) Foreign Application Priority Data

Jan. 5, 2018 (EP) .................................... 18305005

(51) Int. Cl.
*A61K 31/4706* (2006.01)
*A61K 39/395* (2006.01)
(Continued)

(52) U.S. Cl.
CPC ...... *A61K 31/4706* (2013.01); *A61K 39/3955* (2013.01); *A61P 35/00* (2018.01);
(Continued)

(58) Field of Classification Search
None
See application file for complete search history.

(56) References Cited

U.S. PATENT DOCUMENTS

| 3,075,981 A | 1/1963 | Surrey |
| 2006/0194805 A1 | 8/2006 | Bakthavatchalam |

(Continued)

FOREIGN PATENT DOCUMENTS

| CN | 102 249 997 | 11/2011 |
| CN | 102 846 623 | 1/2013 |

(Continued)

OTHER PUBLICATIONS

Burchert et al., "Frequency of CTLA-4 Receptor Ligand (CD86, B7.2)—Positive Plasmacytoid Dendetric Cells Predicts Risk of Disease Recurrence after Ryrosine-Kinase Inhibitor Discontinuation in Chronic Myeloid Leukemia: Results from a Prospective Substudy of the Euroski Trial", *Blood*, 126(23):599 (2015).
Buteau, "Deuterated Drugs: Unexpectedly Nonobvious?", *J. High Tech.* 22 (2009), Abstract.
Lowe et al., "Aggregation, Stability, and Formulation of Human Antibody Therapeutics", *Advances in Protein Chemistry and Structural Biology*, vol. 84, pp. 41-61, (2011).
Smith, "Chiral Toxicology: It's the Same Thing . . . Only Different", *Toxicology Sciences*, 110(1), 4-30 (2009).
Translation of WO2017198196A, downloaded Dec. 15, 2022, 71 pages (2017).
Translation of WO2017198196A claims, downloaded Dec. 15, 2022, 5 pages (2017).

(Continued)

*Primary Examiner* — Bong-Sook Baek
(74) *Attorney, Agent, or Firm* — Parker Highlander PLLC (57) ABSTRACT

The present invention relates to a compound of general formula (I), wherein $R_1$ is $OCH_2CH_2OCH_3$ or $OCH_3$, $R'_1$ is H or OH, $R_2$ is Cl, F, Br or I, with the proviso that when: $R_1$ is $OCH_2CH_2OCH_3$ then $R'_1$ is H, $R_1$ is $OCH_3$ then $R'_1$ is OH, its pharmaceutically acceptable salts and/or optical isomers, tautomers, solvates or isotopic variations thereof. The invention also relates to said compounds for use in the treatment of cancer, namely solid tumor cancer, and preferably those selected from melanoma, colon, lung, pancreas, kidney, Merkel carcinoma, squamous cell carcinoma, prostate, breast and bladder. The invention also relates to a pharmaceutical composition comprising said compounds.

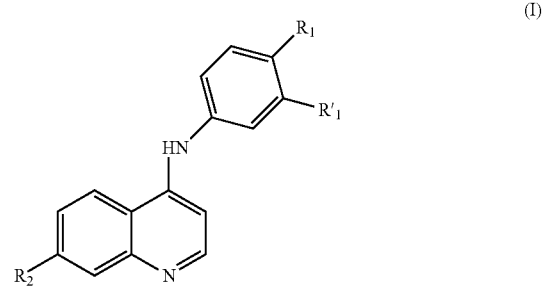

14 Claims, 3 Drawing Sheets

(51) Int. Cl.
| | |
|---|---|
| *A61K 45/06* | (2006.01) |
| *A61P 35/00* | (2006.01) |
| *A61P 35/04* | (2006.01) |
| *C07D 215/44* | (2006.01) |
| *C07K 16/28* | (2006.01) |

(52) U.S. Cl.
CPC ............ *A61P 35/04* (2018.01); *C07D 215/44* (2013.01); *A61K 45/06* (2013.01); *C07K 16/2818* (2013.01); *C07K 16/2827* (2013.01)

(56) References Cited

U.S. PATENT DOCUMENTS

| | | |
|---|---|---|
| 2008/0194557 A1 | 8/2008 | Barbosa et al. |
| 2008/0234267 A1 | 9/2008 | Lackey |
| 2020/0360365 A1 | 11/2020 | Passeron et al. |

FOREIGN PATENT DOCUMENTS

| | | |
|---|---|---|
| CN | 103232444 | 8/2013 |
| JP | 2001500890 A | 9/1997 |
| JP | 2013514320 A | 12/2010 |
| WO | WO 2008/089307 | 7/2008 |
| WO | WO 2011/073322 | 6/2011 |
| WO | WO 2014/130411 | 8/2014 |
| WO | WO2017/198196 | 11/2017 |
| WO | WO 2018/007648 | 1/2018 |
| WO | WO2019/134969 | 7/2019 |
| WO | WO 2019/173482 | 9/2019 |

OTHER PUBLICATIONS

Coimbra, Elaine S. et al., "Amodiaquine analogs, Synthesis and anti-leishmanial activity," Mediterranean Journal of Chemistry, Jan. 1, 2011, pp. 106-113, XP055298745.
Extended European Search Report in EP Application No. 18305005. 3, dated Jul. 2, 2018, 6 pgs.
International Preliminary Report on Patentability in International Application No. PCT/EP2019/050159, dated Jul. 7, 2020, 6 pgs.
International Preliminary Report on Patentability in International Application No. PCT/EP2019/050175, dated Jul. 7, 2020, 6 pgs.
International Search Report and Written Opinion issued in International Application No. PCT/EP2019/050175, dated Apr. 11, 2019.
International Search Report and Written Opinion issued in International Application No. PCT/EP2019/050159, dated Apr. 8, 2019.
Mah et al, "Identification of 4-Phenoxyquinoline Based Inhibitors for L1196M Mutant of Anaplastic Lymphoma Kinase by Structure-Based Design," Journal of Medicinal Chemistry, vol. 6, No. 22, Nov. 22, 2017, pp. 9205-9221, XP055549029.
Otevrel J et al., "Antimycobacterial and photosynthetic electron transport inhibiting activity of ring-substituted 4-arylamino-7-chloroquinolinium chlorides," Molecules: A Journal of Synthetic Organic and Natural Product Chemistry, vol. 18, No. 9, Sep. 2, 2014, pp. 10649-10670, XP002761306.
Office Action for Chinese Application No. 2019800069671.1 dated Feb. 9, 2023, with English translation.
Liu et al., "Synthesis and Anti-Tumor Activities of 4-Anilinoquinoline Derivatives", *Molecules*, 21(21), 2016.
Masarova et al., "Update on Immunotherapy in AML and MDS: Monoclonal Antibodies and Checkpoint Inhibitors Paving the Road for Clinical Practice", *Immunotherapy, Advances in Experimental Medicine and Biology 995, Naing and Hajjar (eds)*, Chapter 4, pp. 97-116, 2018.
Citation 3—Registry [online], Aug. 5, 2010, [retrieved on Apr. 5, 2021], Retrieved from STN, CAS registry No. 1235080-72-4.
Citation 4—Registry [online], Mar. 1, 2007, [Retrieved on Apr. 5, 2021], Retrieved from: STN, CAS registry No. 924143-41-9.
Citation 5—Registry [online], Aug. 4, 2010, [Retrieved on Apr. 5, 2021], Retrieved from: STN, CAS registry No. 1235000-61-9.
Dakshanamurthy et al., "In-silico fragment-based identification of novel angiogenesis inhibitors", Bioorganic & Medicinal Chemistry Letters, vol. 17, No. 16, pp. 4551-4556, Jun. 15, 2007.
Denny; "The 4-anilinoquinazoline class of inhibitors of the erbB family of receptor tyrosine kinases", IL Farmaco, vol. 56, 51-56, 2001.
Lala et al., "Role of nitric oxide in tumor progression: lessons from experimental tumors", *Cancer and Metastasis Reviews*, 17(1), 91-106, 1998.
Golub et al., "Molecular classification of cancer: class discovery and class prediction by gene expression monitoring", *Science*, 286(5439), 531-537, 1999.
Bachy et al., "Anti-PD1 antibody: a new approach to treatment of lymphomas", *Lancet Oncol.* 15(1):7-8, 2014.
Gonzalbes et al., "Hit identification of novel hepranase inhibitors by structure-and ligand-based approaches", *Bioorganic & Medicinal Chemistry*, Pergamon, GB, 21(7), 1944-1951, Jan. 31, 2013.
He et al., "Design of antineoplastic agents based on the '2-phenylnaphthalene-type' structural pattern-synthesis and biological activity stugies of 11H-indolo [3.2-c]quinoline derivatives", *European Journal of Medicinal Chjemi, Editions Scientifique Elsevier*, Paris, FR, 38(1), 101-107, Jan. 1, 2003.
Beauchard et al., Synthesis of original thiazoloindolo[3,2-c]quinoline and novel 8-N-substituted-11H-indolo[3,2-c]quinoline derivatives from benzotriazoles. Part I, *Tetrahedron, Elsevier Science Publishers*, Amsterdam, NL, 62(8), 1895-1903, Feb. 20, 2006.
Meyers et al., "Auto-Tandem Catalysis: Synthesis of Substituted 11H-Indolo[3,2-c]quinolinesvia Palladium-Catalyzed Intermolecular C-N and Intramolecular C-C-Bond Formation", *Advanced Synthesis & Catalysis*, 350(3), 465-470, Feb. 22, 2008.
Sanchez-Martin et al., "Symmetrical Bis-Quinolinium Compounds: New Human Choline Kinase Inhibitors with Antiproliferative Activity against the HT-29 Cell Line", *Journal of Medicinal Chemistry*, 48(9), 3354-3363, May 1, 2005.
Xiang et al., "5-methoxyquinoline derivatives as a new class of EZH2 inhibitors", *Molecules: A Journal of Synthetic Organic and Natural Product Chemi*, M D P IAG, CH, 20(5), 7620-7636, Jan. 1, 2015.

SUBSTITUTED HALO-QUINOLINE DERIVATIVES, METHOD OF PREPARATION AND APPLICATIONS THEREOF

This application is a national phase application under 35 U.S.C. § 371 of International Application No. PCT/EP2019/050175, filed Jan. 4, 2019, which claims benefit of European Application No. 18305005.3, filed Jan. 5, 2018, the entire contents of each of which are hereby incorporated by reference.

FIELD OF THE INVENTION

The invention relates to novel substituted halo-quinoline derivatives which are active for the treatment of cancer.

BACKGROUND OF THE INVENTION

Cutaneous melanoma deriving from the transformation of melanocytes is one of the most lethal cancers among young adults. Its incidence has increased at a dramatic rate during the last decades. Melanoma has a high capability of invasion and rapid metastasis to other organs.

Immune-checkpoint blockades targeting cytotoxic T-lymphocyte-associated protein 4 (CTLA-4), and more recently Programmed Death 1 (PD1) and Programmed Death-Ligand 1 (PDL-1), are recent and major breakthroughs in cancer therapy. Initially developed to treat metastatic melanomas, antibodies against those targets significantly increase overall patient survival and are now being evaluated to treat other solid cancers such as those of the kidney, prostate, colon, and lung. Although anti-PD1 antibodies have shown better results than anti-CTLA-4 antibodies, the response rate remains low (10% to 57%), depending on the cancer type and the treatment combinations. The combination of anti-PD1 and anti-CTLA-4 to treat melanoma has given the best complete response rate so far, 11.5%, but is associated with an almost 70% rate of grade 3 or grade 4 side effects. Few patients therefore benefit from those approaches, and no predictive factor for the response has yet been identified. Accumulating evidence suggests that interferon gamma (IFN-γ) plays a key role in the response to anti-PD1 treatment (1-3). A meta-analysis of all the immune-based approaches to melanoma treatment (including anti-PD1) showed that patients with vitiligoid depigmentation have significantly better rates of progression-free survival and overall survival compared with other patients (4). Furthermore, patients with vitiligo have a threefold lesser risk of developing melanoma (5). An increasing number of data indicate that the IFN-γ/CXCL10 pathway, which is involved in the vitiligoid depigmentation process, plays a key role in determining melanoma risk (6). Thus, the IFN-γ response is implicated as a key factor facilitating the checkpoint-blockade treatment approaches. Inventors of the instant application recently showed that the inhibition of the non-canonical NF-kB pathway, as well as that of the upstream NF-kB-inducing kinase (NIK), restores a senescence program in melanoma cells through decreased EZH2 transcription and significantly reduces tumor growth (7). There are increasing evidences that cellular senescence can trigger or potentiate tumor immune surveillance (8).

The instant invention provides new NIK inhibitors that decrease EZH2 at the transcriptional level and induce the production of an IFN-γ response by the treated cells. These NIK inhibitors reduce the size of subcutaneous tumors without showing any specific toxicity, and when combined with anti-PD1 treatment lead to a dramatic reduction in tumor size with complete regression in some cases. Those effects are associated with a marked increase in the numbers and activation of type M1 macrophages, dendritic cells, Natural killer cells and T-cells within the treated tumors.

SUMMARY OF THE INVENTION

The invention relates to compounds of general formula (I):

in which $R_1$, $R'_1$ and $R_2$ have the meanings indicated below, and to pharmaceutical compositions containing such compounds as well as the uses thereof.

DETAILED DESCRIPTION OF THE INVENTION

The invention relates more particularly to compounds of general formula (I):

wherein
$R_1$ is $OCH_2CH_2OCH_3$ or $OCH_3$,
$R'_1$ is H or OH,
$R_2$ is a halo group selected from chloro (Cl), fluoro (F), bromo (Br) and iodo (I),
with the proviso that when:
$R_1$ is $OCH_2CH_2OCH_3$ then $R'_1$ is H,
$R_1$ is $OCH_3$ then $R'_1$ is OH,
its pharmaceutically acceptable salts and/or optical isomers, tautomers, solvates or isotopic variations thereof.

According to an advantageous embodiment of the invention, the halo group for $R_2$ is chloro (Cl).

The compounds of general formula (I) are more particularly the following:
  7-chloro-N-(4-(2-methoxyethoxy)phenyl)quinolin-4-amine (compound 42) and,
  7-chloro-N-(3-(hydroxy)-4-(methoxy)phenyl)quinolin-4-amine (also named 5-((7-chloroquinolin-4-yl)amino)-2-methoxyphenol) (compound 43).

The compounds of formula (I), their pharmaceutically acceptable salts and/or derived forms (optical isomers, tautomers, solvates or isotopic variations thereof), are valuable pharmaceutically active compounds suitable for the therapy and prophylaxis of various cancers.

The invention thus also pertains to compounds of formula (I) as defined above and, if appropriate, their pharmaceutically acceptable salts and/or optical isomers, tautomers, solvates or isotopic variations thereof, for use in the treatment of cancer, namely solid tumor cancer, and preferably those selected from melanoma, colon, lung, pancreas, kidney, Merkel carcinoma, squamous cell carcinoma, prostate, breast, bladder and lymphomas.

In a particular embodiment, the cancer is melanoma.

The compounds of general formula (I) may be administered alone or in combination. They may also be administered in combination with one or more other drugs.

Generally, they will be administered as a formulation in association with one or more pharmaceutically acceptable excipients or carriers.

The term "excipient" or "carrier" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Another aspect of the invention is thus a pharmaceutical composition comprising a compound of general formula (I) as defined above and optionally a pharmaceutically acceptable carrier.

According to another advantageous embodiment of the invention, the pharmaceutical composition as defined above may additionally comprise:
- at least one immunomodulatory compound, said immunomodulatory compound being preferably an immunomodulatory antibody, and even more preferably an antibody selected from an anti-PD1 antibody, an anti-CTLA4 antibody, an anti-PD-L1 antibody and a mixture of two or more thereof, and/or
- at least one another therapeutic agent.

The term "immunomodulatory compound" refers to a compound that modulates one or more of the components (e.g., immune cells, or subcellular factors, genes regulating immune components, cytokines, chemokines or such molecules) of a host's immune system.

Preferably, the immunomodulatory compound is an immunostimulatory agent. Immunomodulatory agents may include, but are not limited to, small molecules, peptides, polypeptides, fusion proteins, antibodies. Immunomodulatory antibodies are a promising class of anti-cancer therapies, due to their ability to promote a broad and sustained anti-cancer immune response in cancer patients.

Suitable examples of:
- anti-PD1 antibodies are nivolumab, pidilizumab, pembrolizumab, tislelizumab and AMP-514,
- anti-CTLA4 antibodies are ipilimumab,
- anti PD-L1 antibodies are atezolizumab, durvalumab, avelumab, utomilumab and MPDL3280A.

The additional therapeutic agent(s) may also be (a) compound(s) of the formula (I), or a pharmaceutically acceptable salt, derived forms or compositions thereof, or one or more compounds known in the art for the treatment of the conditions listed above.

For example, the additional therapeutic agent will be selected from a different class of therapeutic agents than those of the compounds of formula (I).

Suitable examples of other therapeutic agents which may be used in combination with the compound(s) of formula (I), or pharmaceutically acceptable salts or derived forms thereof, include, but are by no means limited to:
- Anti-cancer agents used for the therapy of cancers such as dacarbazine,
- Nitrosourea alkylating agents, such as fotemustine,
- BRAF inhibitors such as vemurafenib or dabrafenib,
- MEK inhibitors such as trametinib,
- Anti PD1 fusion protein such as AMP-224,
- other immune checkpoint blocking agents or, in general, therapeutic treatments based on immune approaches for treating cancer i.e. biological or chemical compounds or cellular therapies such as adoptive cell therapies, therapeutic cancer vaccines, T/NK cell activating agents.

The invention more particularly relates to a pharmaceutical composition as defined above, as a combined preparation for simultaneous, separate or sequential use in the treatment of cancer, namely solid tumor cancer, and preferably those selected from melanoma, colon, lung, pancreas, kidney, Merkel carcinoma, squamous cell carcinoma, prostate, breast, bladder and lymphomas.

Inasmuch as it may be desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions.

Thus, the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

As previously mentioned, the compounds of the formula (I), or pharmaceutically acceptable salts, derived forms or compositions thereof, can also be used as a combination with one or more additional therapeutic agents to be co-administered to a patient to obtain some particularly desired therapeutic end result such as the treatment of cancers, namely solid tumor cancer, and preferably those selected from melanoma, colon, lung, pancreas, kidney, Merkel carcinoma, squamous cell carcinoma, prostate, breast, bladder and lymphomas.

Preferably, the compounds of the invention, either alone or in combination, are administered to patients at metastatic stage suffering from melanoma, colon, lung, pancreas, kidney, Merkel carcinoma, squamous cell carcinoma, prostate, breast, bladder and lymphomas.

As used herein, the terms "co-administration", "co-administered" and "in combination with", referring to the compounds of formula (I) and one or more other therapeutic agents, is intended to mean, and does refer to and include the following: simultaneous administration of such combination of compound(s) of formula (I) and therapeutic agent(s) to a patient in need of treatment, when such components are formulated together into a single dosage form which releases said components at substantially the same time to said patient, substantially simultaneous administration of such combination of compound(s) of formula (I) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (I) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (I) and therapeutic agent(s) to a patient in need of treatment, when such components are formulated together into a single dosage form which releases said components in a controlled manner whereupon they are concurrently, consecutively, and/or administered at the same and/or different times by said patient, where each part may be administered by either the same or different route.

Compounds of the invention may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

The compounds of the invention may be administered by any suitable route.

Thus, a compound of the invention may be formulated as a pharmaceutical composition for oral, buccal, intranasal, parenteral (e. g. intravenous, intramuscular or subcutaneous), topical or rectal administration or in a form suitable for administration by inhalation or insufflation.

For oral administration, the pharmaceutical composition may take the form of, for example, a tablet or capsule prepared by conventional means with a pharmaceutically acceptable excipient such as a binding agent (e. g., pregelatinized maize starch, polyvinylpyrrolidone or hydroxypropyl methylcellulose); filler (e. g., lactose, microcrystalline cellulose or calcium phosphate); lubricant (e. g., magnesium stearate, talc or silica); disintegrant (e. g., potato starch or sodium starch glycolate); or wetting agent (e. g., sodium lauryl sulphate).

The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional means with a pharmaceutically acceptable additive such as a suspending agent (e. g., sorbitol syrup, methyl cellulose or hydrogenated edible fats); emulsifying agent (e. g., lecithin or acacia); non-aqueous vehicle (e. g., almond oil, oily esters or ethyl alcohol); and preservative (e. g., methyl or propyl p-hydroxybenzoates or sorbic acid).

For buccal administration, the composition may take the form of tablets or lozenges formulated in conventional manner. A compound of the present invention may also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

A compound of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent. Alternatively, the active ingredient may be in powder form for reconstitution with a suitable vehicle, e. g., sterile pyrogen-free water, before use parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

For administration to human patients, the total daily dose of the compounds of the invention is typically in the range 0.001 mg to 5000 or in the range of 0.001 mg to 10000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

It is to be appreciated that all references herein to "treatment" include curative, palliative and prophylactic treatment.

The description, which follows, concerns the therapeutic applications to which the compounds of formula (I) may be put.

A still further aspect of the present invention also relates to the use of the compounds of formula (I), or pharmaceutically acceptable salts, derived forms or compositions thereof, for the manufacture of a drug having an anticancer activity.

In particular, the present inventions concerns the use of the compounds of formula (I), or pharmaceutically acceptable salts, derived forms or compositions thereof, for the manufacture of a drug for the treatment of cancer, namely solid tumor cancer, and preferably those selected from melanoma, colon, lung, pancreas, kidney, Merkel carcinoma, squamous cell carcinoma, prostate, breast, bladder and lymphomas.

As a consequence, the present invention provides a particularly interesting method to treat a mammal, including a human being, with an effective amount of a compound of formula (I) or a pharmaceutically acceptable salt, derived form or composition thereof.

More precisely, the present invention provides a particularly interesting method for the treatment of a cancer disease in a mammal, including a human being, in particular the diseases and/or conditions listed above, comprising administering said mammal with an effective amount of a compound of formula (I), its pharmaceutically acceptable salts and/or derived forms.

The compounds of the formula (I) may be prepared using conventional procedures such as by the following illustrative methods in which the various substituents are as previously defined for the compounds of the formula (I) unless otherwise stated.

Thus compounds of general formula (I) can be prepared starting from the corresponding 4-chloro-7-haloquinoline by an aromatic nucleophilic substitution with appropriate amine:

Compounds of general formula (I) wherein $R_2$=fluoro or bromo, can be prepared starting from the corresponding 4-chloro-7-haloquinoline, according to the previously reported procedures (see for examples: *Bioorg. Med. Chem.* 2013, 21 (11), 3147-3153; *J. Med. Chem.*, 2015, 58 (14), 5522-5537).

Pharmaceutically acceptable salts of the compounds of formula (I) include the acid addition and base salts thereof.

Suitable acid addition salts are formed from acids, which form non-toxic salts.

Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate and xinafoate salts.

Suitable base salts are formed from bases, which form non-toxic salts.

Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:

(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of the invention may exist in both unsolvated and solvated forms.

The term "solvate" is used herein to describe a molecular complex comprising the compound of the invention and a stoichiometric amount of one or more pharmaceutically acceptable solvent molecules, for example, ethanol.

The term "hydrate" is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components, which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called "pro-drugs" of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "pro-drugs". Further information on the use of pro-drugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Pro-drugs in accordance with the invention can, for example, be produced by replacing appropriate functionalities present in the compounds of formula (I) with certain moieties known to those skilled in the art as "pro-moieties" as described, for example, in "Design of Prodrugs" by H. Bundgaard (Elsevier, 1985).

Some examples of prodrugs in accordance with the invention include for example where the compound of formula (I) contains an alcohol functionality (—OH), a compound wherein the hydrogen of the alcohol functionality of the compound of formula (I) is replaced by (C1-C6) alkanoyloxymethyl.

Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug.

Some examples of metabolites in accordance with the invention include where the compound of formula (I) contains a phenol moiety.

Compounds of formula (I) containing one or more asymmetric carbon atoms can exist as two or more stereoisomers. Included within the scope of the present invention are all stereoisomers, geometric isomers and tautomeric forms of the compounds of formula (I), including compounds exhibiting more than one type of isomerism, and mixtures of one or more thereof.

Also included is acid addition or base salts wherein the counter ion is optically active, for example, D-lactate or L-lysine, or racemic, for example, DL-tartrate or DL-arginine.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC (chiral columns), on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. For reverse HPLC $CH_3CN$ and $H_2O$, MeOH or iPrOH and $H_2O$ are used as solvents. Concentration of the eluate affords the enriched mixture.

Stereoisomeric conglomerates may be separated by conventional techniques known to those skilled in the art-see, for example, "Stereochemistry of Organic Compounds" by E. L. Eliel (Wiley, New York, 1994). "Chiral Separation Techniques". by G. Subramanian. John Wiley & Sons, 2008. "Preparative Enantioselective Chromatography" by G. B. Cox. Wiley, 2005.

Pharmaceutically acceptable solvates in accordance with the invention include those wherein the solvent of crystallization may be isotopically substituted, e.g. $D_2O$.

The following examples illustrate the preparation of the compounds of the formula (I) and their pharmacological properties.

EXAMPLE 1

Preparation of Compounds (I) of the Invention

Compounds 42 and 43 were prepared according to the procedure below.

7-chloro-N-(4-(2-methoxyethoxy)phenyl)quinolin-4-amine (Compound 42)

A mixture of 4,7-dichloroquinoline (1 mmol, 1 eq) and 4-(2-methoxyethoxy)aniline (1 mmol, 1 eq) in ethanol was subjected to microwave irradiation at 80° C. for 1 h. The mixture was cooled to room temperature before addition of ethyl acetate, the resulting precipitate was collected, wash with ethyl acetate and diethyl ether to afford pure product without any further purifications.

7-chloro-N-(4-(2-methoxyethoxy)phenyl)quinolin-4-amine
Chemical Formula: $C_{18}H_{17}ClN_2O_2$
Exact Mass: 328,0979
Molecular Weight: 328,7960

$^1$H NMR (400 MHz, DMSO-$d_6$) δ 14.79 (s, 1H), 11.13 (s, 1H), 8.87 (d, J=9.1 Hz, 1H), 8.49 (d, J=7.1 Hz, 1H), 8.18 (d, J=2.2 Hz, 1H), 7.86 (dd, J=9.1, 2.1 Hz, 1H), 7.40 (d, J=8.9 Hz, 2H), 7.14 (d, J=8.9 Hz, 2H), 6.65 (d, J=7.0 Hz, 1H), 4.21-4.13 (m, 2H), 3.75-3.67 (m, 2H), 3.34 (s, 3H).

$^{13}$C NMR (101 MHz, DMSO) δ 157.2, 154.8, 142.6, 138.5, 137.76, 128.9, 126.7, 126.6, 125.6, 118.6, 115.2, 115.12, 99.5, 69.8, 66.7, 57.7.

MS: ESI (m/z): [M+H]$^+$ calcd for $C_{18}H_{17}ClN_2O_2$ 329.09. found 329.32.

HPLC: Purity $\lambda_{254}$: 99.4%, tR: 3.54

7-chloro-N-(3-(hydroxy)-4-(methoxy)phenyl)quinolin-4-amine (Compound 43) (Also Named 5-((7-chloroquinolin-4-yl)amino)-2-methoxyphenol)

A mixture of 4,7-dichloroquinoline (1 mmol, 1 eq) and 5-amino-2-methoxyphenol (1 mmol, 1 eq) in ethanol was subjected to microwave irradiation at 80° C. for 1 h. The mixture was cooled to room temperature before addition of ethyl acetate, the resulting precipitate was collected, wash with ethyl acetate and diethyl ether to afford pure product without any further purifications.

5-((7-chloroquinolin-4-yl)amino)-2-methoxyphenol
Chemical Formula: $C_{16}H_{13}ClN_2O_2$
Exact Mass: 300,0666
Molecular Weight: 300,7420

$^1$H NMR (400 MHz, DMSO-$d_6$) δ 14.41 (s, 1H), 10.88 (s, 1H), 9.56 (s, 1H), 8.76 (d, J=9.2 Hz, 1H), 8.49 (d, J=7.0 Hz, 1H), 8.10 (d, J=2.1 Hz, 1H), 7.86 (dd, J=9.1, 2.1 Hz, 1H), 7.09 (d, J=8.4 Hz, 1H), 6.91-6.81 (m, 2H), 6.72 (d, J=7.0 Hz, 1H), 3.84 (s, 3H).

$^{13}$C NMR (101 MHz, DMSO) δ 154.7, 147.1, 146.7, 142.5, 138.5, 137.7, 129.0, 126.6, 125.5, 118.6, 115.7, 115.2, 112.4, 112.3, 99.6, 55.3.

MS: ESI (m/z): [M+H]$^+$ calcd for $C_{16}H_{13}ClN_2O_2$ 301.06. found 301.14.

HPLC: Purity $\lambda_{254}$: 99.0%, tR: 3.21

EXAMPLE 2

In Vitro Activity of Compounds 42 and 43 of the Invention

Material and Methods

Cancer Cell Proliferation Assay (A375, A549, PC3, HT-29, MiaPaca-2 and MCF-7)

The tested cancer cells are the following: human melanoma cells (A375), lung carcinoma cells (A549), prostate cancer cells (PC3), colon adenocarcinoma (HT29), pancreas carcinoma (MiaPaca 2) and breast carcinoma (MCF-7).

Cells were counted using a Malassez chamber. The average and standard deviation were calculated from triplicate experiments. Antiproliferative effects were evaluated by trypan blue exclusion assay. Briefly, cells were seeded into 12-well plate and grown in media supplemented with indicated compound at 1 or 10 μM for 48 h or 96 h. Cells were washed with PBS and detached by trypsinization, collected and colored by trypan blue.

Dead and living cells were counted and proliferation was calculated as follow: Proliferation (%)=[(treated cell number/untreated cells number)*100].

As a comparison, cell viability was also determined and calculated as follow: Viability (%)=100−[(dead cell number/total cells)*100].

Results obtained are summarized in Tables 1a (viability) and 1b (proliferation).

Melanocyte Viability Assay (MHN)

Cell viability effects were evaluated by trypan blue exclusion assay. Briefly, cells were seeded into 12-well plate and grown in media supplemented with indicated compound at 10 μM for 96 h. Cells were washed with PBS and detached by trypsinization, collected and colored by trypan blue. Dead and living cells were counted and cell viability was calculated as follow: Viability (%)=100−[(dead cell number/total cells)*100].

Results obtained are summarized in Table 2.

Quantitative RT-PCR Analysis of EZH2 and p21 Gene Expression

Total RNA was isolated from cells using the RNAeasy minikit (Qiagen) according to the manufacturer's procedure. Reverse transcription was performed using the AMV reverse transcription system (Promega), and quantitative PCR was performed with Power Sybr green (Applied Biosystems, Life Technologies, Grand Island, NY) following the manufacturer's instructions. The PCR was carried out on a Step One plus Real-Time PCR system (Applied Biosystems). All analyses were done in triplicate, and a melting curve analysis was performed to control for product quality and specificity. Expression levels were calculated using the comparative method of relative quantification, with SB34 as a normalizer. The data were analyzed for statistical significance using Student's t-test. The results are presented as the mean±SEM relative to the control.

PCR primers for EZH2 (accession number NM004456.4) and p21 (CDKN1A) (accession number NM078467.2) were obtained from primer bank or primer depot (http://pga.mgh.harvard.edu/primerbank/, https://primerdepot.nci.nih.gov), and their specificity was verified using primer blast (http://www.ncbi.nlm.nih.gov/tools/primer-blast/).

Figure 1:
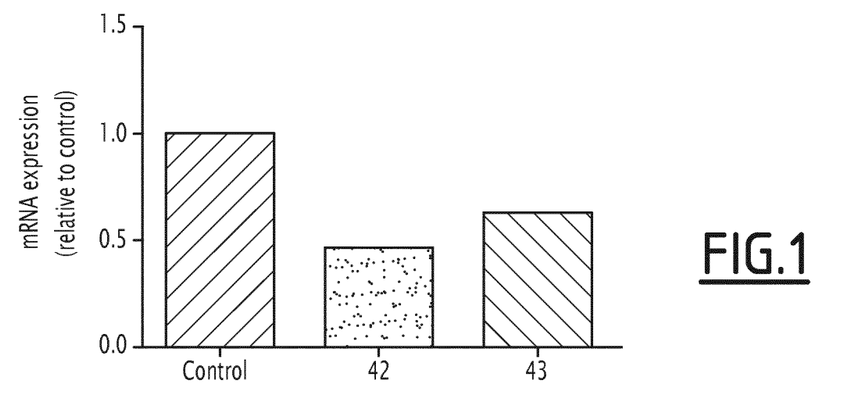
FIG. 1: mRNA levels of EZH2 detected by qPCR in A375 cancer cells incubated with compound 42, 43 (10 μM) or DMSO (control) for 96 h.
Figure 2:
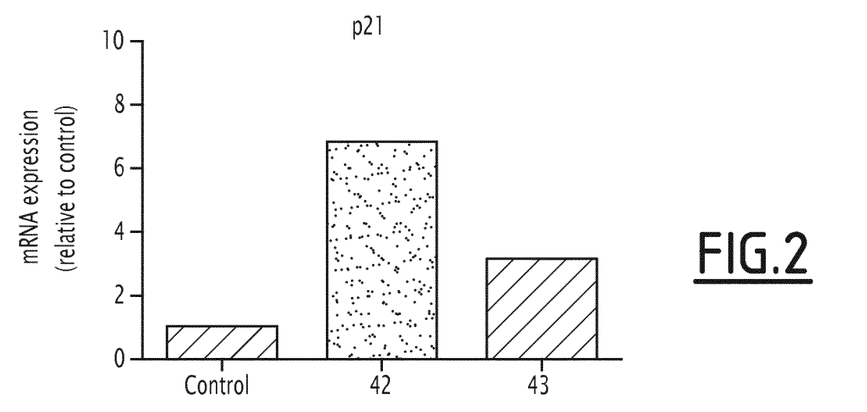
FIG. 2: mRNA levels of p21 detected by qPCR in A375 cancer cells incubated with compound 42, 43 (10 μM) or DMSO (control) for 96 h.

Results obtained are summarized in Table 3 and FIGS. 1 (EZH2) and 2 (p21).

ELISA Measurement

Supernatant from cells treated for 96 h was tested for human or mouse IFN-γ content via ELISA (peprotech, cat 900-k27 and 900-k98) kit following the manufacturer's instructions.

Figure 3:
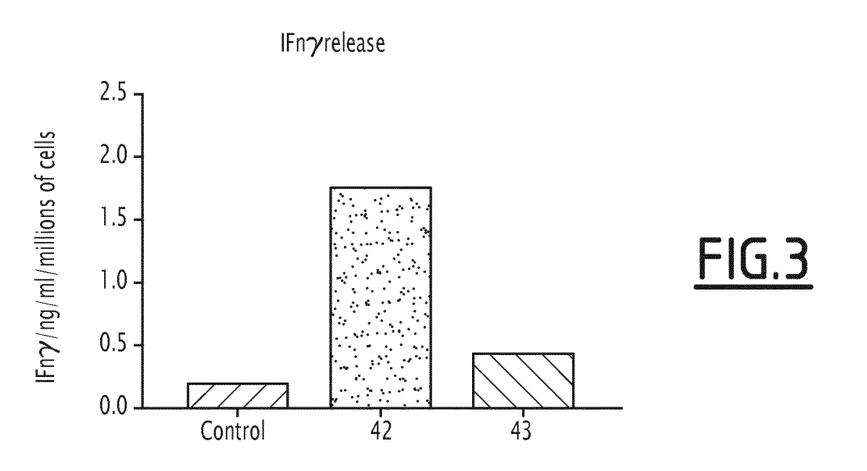
FIG. 3: IFN-γ levels detected by ELISA in supernatant of A375 cancer cells treated with compound 42, 43 (10 μM) or DMSO (control) for 96 h.

Results obtained are summarized in Table 4 and FIG. 3.

Quantitative Senescence-Associated Beta-Galactosidase Assay

The activity of senescence-associated β-galactosidase (SA-β-Gal) in cell extracts was quantified by measuring the cleavage of 4-methylumbelliferyl-β-D-galactopyranoside (4-MUG), which does not fluoresce until cleaved by the enzyme to generate the fluorophore 4-methylumbelliferone. The production of the fluorophore was monitored at an emission/excitation wavelength of 365/460 nm, as reported (Gary and Kindell, 2005)

Results obtained are summarized in Table 5.

Microsomal Stability (Mouse Liver Microsomes)

Microsomal stability was evaluated with mouse liver microsomes (0.5 mg/mL) and NADPH cofactor (1 mM) at 37° C. The percentage of remaining compound is determined at 5 min by LC-MS by measuring the area under the peak of compound on the chromatogram.

Results obtained are summarized in Table 6.

Results and Conclusions

The results obtained are summarized in Tables 1a, 1b, 2 to 6.

TABLE 1a viability

| | Cancer Cell Viability (% à 10 μM)* | | | | | |
|---|---|---|---|---|---|---|
| Tested compounds | A375 | A549 | PC3 | HT29 | MiaPaca-2 | MCF-7 |
| Compound 42 | 99.3 | 99.7 | 98.9 | 97.3 | 100.0 | 97.2 |
| Compound 43 | 95.8 | 99.8 | 94.6 | 85.8 | 97.6 | 99.6 |

*Viability normalized to DMSO-treated control

TABLE 1b proliferation

| Tested compounds | Cancer Cell Proliferation (% à 10 μM)* | | | | | |
|---|---|---|---|---|---|---|
| | A375 | A549 | PC3 | HT29 | MiaPaca-2 | MCF-7 |
| Compound 42 | 6.9 | 19.5 | 14.1 | 3.5 | 7.8 | 11.9 |
| Compound 43 | 30.5 | 51.1 | 55.0 | 15.6 | 32.4 | 29.5 |

*Proliferation normalized to DMSO-treated control

Table 1a shows that compounds 42 and 43 do not significantly affect the viability of treated cancer cells compared to untreated ones.

On the other hand, Table 1b shows that compounds 42 and 43, and more particularly compound 42, strongly reduce the proliferation of all tested cancer cells (human melanoma cells (A375), lung carcinoma cells (A549), prostate cancer cells (PC3), colon adenocarcinoma (HT29), pancreas carcinoma (MiaPaca 2) and breast carcinoma (MCF-7).

No decrease in viability is observed at early time points (up to 96 h). The compounds provide a non-competitive inhibition on NIK leading to a strong selectivity without off target effects that is observed with competitive NIK inhibitors (9). By its action on EZH2, the inhibition of NIK leads to a demethylation of several key genes involved in cell cycle such as p21 and thus increases its expression. As a consequence, the proliferation of all treated cells tested so far is strongly reduced (from 55% to 3.5% depending on the compound and the cell line).

TABLE 2 melanocytes viability

| Tested compounds | Heathly Cell Viability (% à 10 μM)* MHN |
|---|---|
| Compound 42 | 99.0 |
| Compound 43 | 95.8 |

*Viability normalized to DMSO-treated control

Table 2 shows that compounds 42 and 43 do not significantly affect the viability of human melanocytes.

NIK and the downstream target EZH2 are not expressed or at very low level in normal cells. Thus, the selective inhibition of NIK by the compounds of the invention do not alter normal cells and do not modify the viability of normal cells such as melanocytes.

TABLE 3

Quantitative RT-PCR analysis

| | qPCR* | |
|---|---|---|
| Tested compounds | EZH2 A375 | p21 A375 |
| Compound 42 | 0.23 | 6.79 |
| Compound 43 | 0.62 | 3.08 |

*mRNA (fold relative to DMSO-treated control)

Table 3 shows that incubation of cells with compound 42 leads to a drastic decrease of mRNA expression of EZH2 as compared to incubation with a control compound (DMSO) (FIG. 1). Correspondingly treatment with compound 42 leads to a major increase of p21 mRNA expression (FIG. 2).

A more modest decrease of EZH2 mRNA expression was observed when cells were treated with compound 43, together with a significant increase of p21 mRNA expression.

Compounds 42 and 43 act by inhibiting NIK that regulates the non-canonical NF-kB pathway which in turn transcriptionally inhibits EZH2.

EZH2 is the central target as it decreases p21 by promoting its methylation and inhibit the transcription of IFN-γ by direct interaction on its promoter.

By decreasing EZH2 transcription, the compounds of the invention increase p21 and promote senescence. It thus induces a decrease in proliferation of treated cells. The immune activation is due to the induced secretion of IFN-γ by the treated cells.

TABLE 4

Elisa measurements

| Tested compounds | ELISA IFN-γ (A375)* |
|---|---|
| DMSO control | 0.17 |
| Compound 42 | 1.73 |
| Compound 43 | 0.41 |

*IFN-γ concentration (ng/mL)/millions cells

Table 4 demonstrates that A375 cells treated with the compounds 42 and 43, and particularly compound 42, produce and secrete IFN-γ while almost no IFN-γ can be detected in untreated cells (FIG. 3).

EZH2 inhibits the production of IFN-γ by interfering directly on its promotor site. By downregulating EZH2 at its transcriptional level the compounds induce the transcription of IFN-γ and its production by the treated cancer cells. Table 4 shows a marked increase of the secretion of IFN-γ in the media by the treated cancer cells as compared to control. This local production of IFN-γ is crucial for attracting and activating the immune cells that will in vivo participate to the elimination of the cancer cells.

TABLE 5

Quantitative senescence-associated beta-galactosidase assay

| Tested compounds | % Senescence* |
|---|---|
| Compound 42 | 645.9 |
| Compound 43 | 1875.1 |

*conversion rate (fold relative to DMSO-treated control)

The inhibition of the non-canonical NFkB pathway has been shown to decrease EZH2 and to restore a senescence program by decreasing the methylation of p21 and thus increasing its expression (9). Table 5 shows that the compounds of the invention (that inhibits the non-canonical NFkB pathway by selectively inhibiting NIK) induces a marked increase of senescence in the treated cells as compared to control. This increase senescence is in accordance with the increase expression of p21 shown in table 3.

TABLE 6

Microsomal stability

| Tested compounds | Microsomal stability, mouse liver (5 min)* |
|---|---|
| Compound 42 | 21% ± 3 |
| Compound 43 | 41% ± 3 |

*Percentage of the remaining compound after 5 min of incubation with microsomes

Table 6 shows that compound 43 exhibits high microsomal stability compared to 42 (41% versus 21%). Microsomal stability serves as an in vitro assessment for the

EXAMPLE 3

In Vitro Activity of Compounds 42 and 43 of the Invention

The melanoma cell line A375 was treated during 96 h with graded concentration of compounds 42 and 43. At the end of the culture period, the cell concentration was determined.

Figure 4:
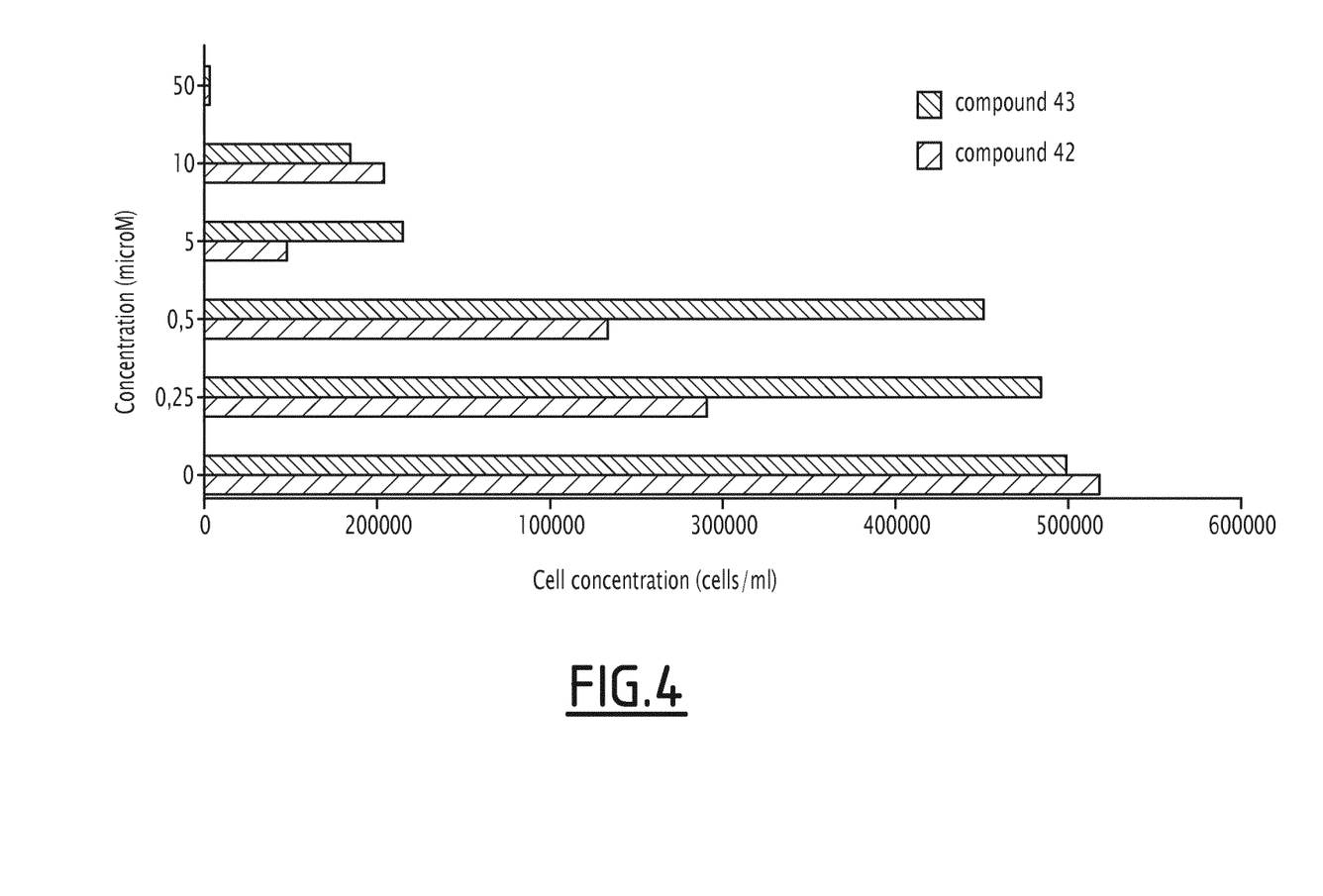
FIG. 4: in vitro dose response study with compounds 42 and 43.

Results demonstrate an inhibition of A375 proliferation starting around 5 mM of compounds 42 and 43 (see FIG. 4).

Compound 42 has an IC50 of 0.42 µM and compound 43 of 1.83 µM.

EXAMPLE 4

In Vivo Activity of Compounds 42 of the Invention

B9 melanoma cells were administrated subcutaneously.

Compound 42 was administrated IP once every day at 50 mg/kg. The anti-PD1 compound (BE0146-clone RMP1-14) was administered IP once every day at 10 mg/kg.

Administration of treatment was made when tumor are visible (between 50 and 100 mm$^3$).

Figure 5:
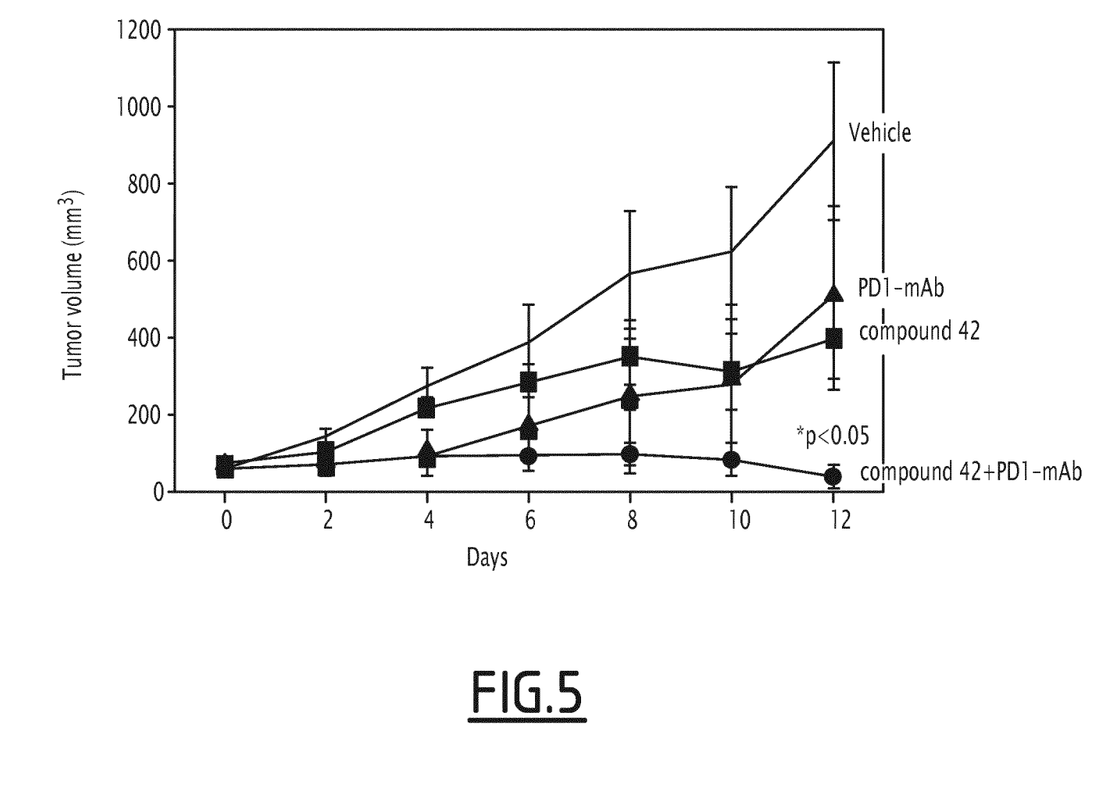
FIG. 5: in vivo effect of compound 42 alone or in combination with an anti-PD-1 antibody.

The results are shown in FIG. 5.

REFERENCES

Throughout this application, various references describe the state of the art to which this invention pertains. The disclosures of these references are hereby incorporated by reference into the present disclosure.

1. J. Fu, I. J. Malm, D. K. Kadayakkara, H. Levitsky, D. Pardoll, Y. J. Kim, Preclinical evidence that PD1 blockade cooperates with cancer vaccine TEGVAX to elicit regression of established tumors. *Cancer research* 74, 4042-4052 (2014).
2. T. Bald, J. Landsberg, D. Lopez-Ramos, M. Renn, N. Glodde, P. Jansen, E. Gaffal, J. Steitz, R. Tolba, U. Kalinke, A. Limmer, G. Jonsson, M. Holzel, T. Tuting, Immune cell-poor melanomas benefit from PD-1 blockade after targeted type I IFN activation. *Cancer discovery* 4, 674-687 (2014).
3. Z. Guo, H. Wang, F. Meng, J. Li, S. Zhang, Combined Trabectedin and anti-PD1 antibody produces a synergistic antitumor effect in a murine model of ovarian cancer. *J Transl Med* 13, 247 (2015).
4. H. E. Teulings, J. Limpens, S. N. Jansen, A. H. Zwinderman, J. B. Reitsma, P. I. Spuls, R. M. Luiten, Vitiligo-like depigmentation in patients with stage III-IV melanoma receiving immunotherapy and its association with survival: a systematic review and meta-analysis. *J Clin Oncol* 33, 773-781 (2015).
5. H. E. Teulings, M. Overkamp, E. Ceylan, L. Nieuweboer-Krobotova, J. D. Bos, T. Nijsten, A. W. Wolkerstorfer, R. M. Luiten, J. P. van der Veen, Decreased risk of melanoma and nonmelanoma skin cancer in patients with vitiligo: a survey among 1307 patients and their partners. *Br J Dermatol* 168, 162-171 (2013).
6. M. Rashighi, P. Agarwal, J. M. Richmond, T. H. Harris, K. Dresser, M. W. Su, Y. Zhou, A. Deng, C. A. Hunter, A. D. Luster, J. E. Harris, CXCL10 is critical for the progression and maintenance of depigmentation in a mouse model of vitiligo. *Sci Transl Med* 6, 223ra223 (2014).
7. G. M. De Donatis, E. L. Pape, A. Pierron, Y. Cheli, V. Hofman, P. Hofman, M. Allegra, K. Zahaf, P. Bahadoran, S. Rocchi, C. Bertolotto, R. Ballotti, T. Passeron, NF-kB2 induces senescence bypass in melanoma via a direct transcriptional activation of EZH2. *Oncogene*, (2015).
8. T. W. Kang, T. Yevsa, N. Woller, L. Hoenicke, T. Wuestefeld, D. Dauch, A. Hohmeyer, M. Gereke, R. Rudalska, A. Potapova, M. Iken, M. Vucur, S. Weiss, M. Heikenwalder, S. Khan, J. Gil, D. Bruder, M. Manns, P. Schirmacher, F. Tacke, M. Ott, T. Luedde, T. Longerich, S. Kubicka, L. Zender, Senescence surveillance of premalignant hepatocytes limits liver cancer development. *Nature* 479, 547-551 (2011).
9. De Donatis G M, Le Pape E, Pierron A, Cheli Y, Hofman V, Hofman P, Allegra M, Zahaf K, Bahadoran P, Rocchi S, Bertolotto C, Ballotti R, Passeron T. NF-kB2 induces senescence bypass in melanoma via a direct transcriptional activation of EZH2. *Oncogene* 35 (21): 2813 (2016 May).

The invention claimed is:

1. A compound of general formula (I):

wherein
$R_1$ is $OCH_2CH_2OCH_3$ or $OCH_3$,
$R'_1$ is H or OH,
$R_2$ is Cl, F, Br or I,
with the proviso that when:
$R_1$ is $OCH_2CH_2OCH_3$ then $R'_1$ is H,
$R_1$ is $OCH_3$ then $R'_1$ is OH,
or a pharmaceutically acceptable salt thereof.

2. A compound according to claim 1 wherein $R_2$ is Cl.

3. A compound according to claim 1 which is selected from:
7-chloro-N-(4-(2-methoxyethoxy)phenyl)quinolin-4-amine and
7-chloro-N-(3-(hydroxy)-4-(methoxy)phenyl)quinolin-4-amine;
or a pharmaceutically acceptable salt thereof.

4. A method for the treatment of cancer, the method comprising administering a compound according to claim 1 to a patient in need thereof.

5. A pharmaceutical composition comprising:
a compound as defined in claim 1,
optionally at least one pharmaceutically acceptable carrier.

6. A pharmaceutical composition according to claim 5, additionally comprising:
at least one immunomodulatory compound, and/or
at least one one other therapeutic treatment.

7. A pharmaceutical composition according to claim 6, wherein the other therapeutic treatment is chosen from anti-cancer agents, nitrosourea alkylating agents, BRAF inhibitors, MEK inhibitors, anti PD1 fusion protein, adoptive cell therapies, therapeutic cancer vaccines, and T/NK cell activating agents.

8. A pharmaceutical composition according to claim 6, wherein the pharmaceutical composition is provided as a combined preparation.

9. A compound according to claim 1, wherein said compound is 7-chloro-N-(4-(2-methoxyethoxy)phenyl)quinolin-4-amine, or a pharmaceutically acceptable salt thereof.

10. A compound according to claim 1, wherein said compound is 7-chloro-N-(3-(hydroxy)-4-(methoxy)phenyl)quinolin-4-amine, or a pharmaceutically acceptable salt thereof.

11. A method according to claim 4, wherein the cancer is a solid tumor cancer.

12. A method according to claim 4, wherein the cancer is melanoma, colon cancer, lung cancer, pancreas cancer, kidney cancer, Merkel carcinoma, squamous cell carcinoma, prostate cancer, breast cancer, or bladder cancer.

13. A pharmaceutical composition according to claim 6, wherein said immunomodulatory compound is an immunomodulatory antibody.

14. A pharmaceutical composition according to claim 13, wherein said antibody is an anti-PD1 antibody, an anti-CTLA4 antibody, an anti-PD-L1 antibody, or a mixture of two or more thereof.

\* \* \* \* \*